United States Patent [19]

Biller

[11] Patent Number: 4,924,024

[45] Date of Patent: May 8, 1990

[54] PHOSPHORUS-CONTAINING SQUALENE SYNTHETASE INHIBITORS, NEW INTERMEDIATES AND METHOD

[75] Inventor: Scott A. Biller, Ewing, N.J.

[73] Assignee: E. R. Squibb & Sons, Inc., Princeton, N.J.

[21] Appl. No.: 359,606

[22] Filed: Jun. 1, 1989

Related U.S. Application Data

[62] Division of Ser. No. 141,744, Jan. 11, 1988, Pat. No. 4,871,721.

[51] Int. Cl.$^5$ .............................. C07F 9/38; C07F 9/42
[52] U.S. Cl. ...................................... 558/202; 558/207
[58] Field of Search ................................. 558/202, 207

[56] References Cited

PUBLICATIONS

Araki et al., "Current Abstracts of Chemistry", vol. 103, Issue 1199, (1986), No. 394994.

Poulter, C. D. et al., Biosynthesis of Isoprenoid Compounds, "Conversion of Farnesyl Pyrophosphate to Squalene", vol. 1, Chapter 8, pp. 413–441, J. Wiley and Sons, 1981.

Faust, J. R., et al., Proc. Nat. Acad. Sci., USA, "Squalene Synthetase Activity in Human Fibroblasts: Regulation via the Low Density Lipoprotein Receptor", 1979, 76, 5018–5022.

de Montellano, P. Ortiz, et al., J. Med. Chem., "Inhibition of Squalene Synthetase by Farnesvl Pyrophosphate Analogues", 1977, 20, 243–249.

Corey and Volante, J. Am. Chem. Soc., "Application of Unreactive Analogs of Terpenoid Pyrophosphates to Studies of Multistep Biosynthesis, Demonstration that 'Presqualene Pyrophosphate' is an Essential Intermediate on the Path to Squalene", 1976, 98, 1291–3.

Sandifier, R. M. et al., J. Am. Chem. Soc., 1982, 104, 7376–8, "Squalene Synthetase, Inhibition by an Ammonium Analogue of a Carbocationic Intermeidate in the Conversion of Presqualene Pyrophosphate to Squalene".

Bertolino, A., et al., Biochim. Biophys. Acta., 1978, 530, 17–23, "Polyisoprenoid Amphiphilic Compounds as Inhibitors of Squalene Synthesis and Other Microsomal Enzymes".

Poulter, C. D. et al., J. Org. Chem., 1986, 51, 4768–4779, "Phosphorylation of Isoprenoid Alcohols".

Poulter, C. D., et al., J.A.C.S., 1987, 109, 5542, "Methane and Difluoromethanediphosphonate Analogues of Geranyl Diphosphate: Hydrolysis–Inert Alternate Substrates".

McClard, R. W., et al., J. Am. Chem. Soc., 1987, 109, 5544–5545, "Novel Phosphonylphosphinyl (P-C-P-C) Analogues of Biochemically Interesting Diphosphates, Syntheses and Properties of P-C-P-C Analogues of Isophentenyl Diphosphate and Dimethylallyl Diphosphate".

Capson, T. L., PhD Dissertation, Jun. 1987, Dept. of Medicinal Chemistry, The University of Utah, Abstract, Table of Contents, pp. 16, 17, 40–43, 48–51, Summary.

Primary Examiner—Anton H. Sutto
Attorney, Agent, or Firm—Burton Rodney

[57] ABSTRACT

Compounds which are useful as inhibitors of cholesterol biosynthesis and thus as hypocholesterolemic agents are provided which have the structure $$CH_3-\underset{\underset{CH_3}{|}}{C}=CH-CH_2-CH_2-\underset{\underset{CH_3}{|}}{C}=CH-Q-Z-\underset{\underset{OR^1}{|}}{\overset{\overset{O}{\|}}{P}}-\underset{\underset{R^3}{|}}{\overset{\overset{R^2}{|}}{C}}-\underset{\underset{OR^{1a}}{|}}{\overset{\overset{O}{\|}}{P}}-OR$$

wherein
Q is $$\{(CH_2)_2-\underset{\underset{CH_3}{|}}{C}=CH\}$$

or a bond;

Z is $-(CH_2)_n-$ or $-(CH_2)_p-CH=CH-(CH_2)_m-$, wherein n is 1 to 5; p is 0, 1 or 2; m is 0, 1 or 2;

R, $R^1$ and $R^{1a}$ are the same or different and are H, lower alkyl or a metal ion; and $R^2$ and $R^3$ may be the same or different and are H or halogen.

New intermediates used in preparing the above compounds and method for preparing same, pharmaceutical compositions containing such compounds and a method for using such compounds to inhibit cholesterol biosynthesis are also provided.

3 Claims, No Drawings

PHOSPHORUS-CONTAINING SQUALENE SYNTHETASE INHIBITORS, NEW INTERMEDIATES AND METHOD

This is a division of application Ser. No. 141,744, filed Jan. 11, 1988, now U.S. Pat. No. 4,871,721.

FIELD OF THE INVENTION

The present invention relates to new phosphorus-containing compounds which inhibit the activity of squalene synthetase and thus are useful in inhibiting cholesterol biosynthesis, to hypocholesterolemic compositions containing such compounds, to a method of using such compounds for inhibiting cholesterol biosynthesis, to new intermediates formed in the preparation of such compounds and to a method for preparing such compounds.

BACKGROUND OF THE INVENTION

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling, H. C., in "Biosynthesis of Isoprenoid Compounds", Vol. I, Chapter 8, pp. 413-441, J. Wiley and Sons, 1981 and references therein). This enzyme is the first committed step of the de novo cholesterol biosynthetic pathway. The selective inhibition of this step should allow the essential pathways to isopentenyl tRNA, ubiquinone, and dolichol to proceed unimpeded. Squalene synthetase, along with HMG-CoA reductase has been shown to be down-regulated by receptor mediated LDL uptake (Faust, J. R.; Goldstein, J. L.; Brown, M. S. *Proc. Nat. Acad. Sci. USA*, 1979, 76, 5018-5022), lending credence to the proposal that inhibiting squalene synthetase will lead to an up-regulation of LDL receptor levels, as has been demonstrated for HMG-CoA reductase, and thus ultimately should be useful for the treatment and prevention of hypercholesterolemia and atheroschlerosis.

One approach to inhibitors of squalene synthetase is to design analogs of the substrate FPP. It is clear from the literature that the pyrophosphate moiety is essential for binding to the enzyme. However, such pyrophosphates are unsuitable as components of pharmacological agents due to their chemical and enzymatic lability towards allylic C-O cleavage, as well as their susceptibility to metabolism by phosphatases.

P. Ortiz de Montellano et al in *J. Med. Chem.*, 1977, 20, 243-249 describe the preparation of a series of substituted terpenoid pyrophosphate (Table A), and have shown these to be competitive inhibitors of the squalene synthetase enzyme. These substances retain the unstable allylic pyrophosphate moiety of FPP.

TABLE A

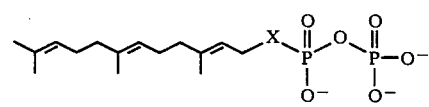

| No. | X | Y | Z |
|---|---|---|---|
| 1 | CH₃ | CH₃ | H |
| 2 | H | H | H |
| 3 | C₂H₅ | H | H |
| 4 | I | H | H |
| 5 | H | I | H |

TABLE A-continued

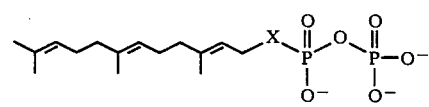

| No. | X | Y | Z |
|---|---|---|---|
| 6 | CH₃ | H | SCH₃ |

Corey and Volante, *J. Am. Chem. Soc.* 1976, 98, 1291-3, have prepared FPP analog A and presqualene pyrophosphate (PSQ-PP) analog B as inhibitors of squalene biosynthesis. (Presqualene pyrophosphate is an intermediate in the conversion of FPP to squalene). These inhibitors possess methylene groups in place of the allylic oxygen moiety of FPP and PSQ-PP, but still retain the chemically and enzymatically unstable pyrophosphate linkage.

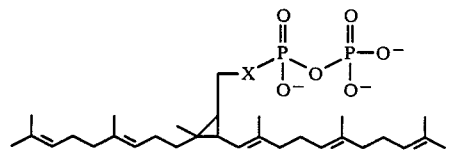

A    X = CH₂
FPP  X = O

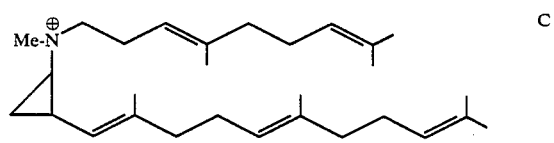

B       X = CH₂
PSQ—PP  X = O

Poulter and co-workers have prepared cyclopropane C (Sandifer, R. M., et al., *J. Am. Chem. Soc.* 1982, 104, 7376-8) which in the presence of inorganic pyrophosphate is an intermediate analog inhibitor of the enzyme squalene synthetase.

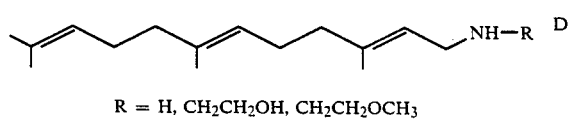

Altman and co-workers, Bertolino, A, et al., *Biochim. Biophys. Acta.* 1978, 530, 17-23, reported that farnesyl amine and related derivatives D inhibit squalene synthetase, but provide evidence that this inhibition is non-specific and probably related to membrane disruption.

R = H, CH₂CH₂OH, CH₂CH₂OCH₃

DESCRIPTION OF THE INVENTION

In accordance with the present invention, there is provided phosphorus-containing compounds which inhibit the enzyme squalene synthetase and thus are useful as hypocholesterolemic agents and have the following structure

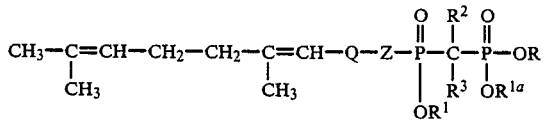

wherein
Q is

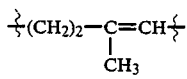

or a bond;
Z is —(CH$_2$)$_n$— or —(CH$_2$)$_p$—CH=CH—(CH$_2$)$_m$—, wherein n is 1 to 5; p is 0, 1 or 2; m is 0, 1 or 2;

R, R$^1$ and R$^{1a}$ may be the same or different and are H, lower alkyl or a metal ion; and R$^2$ and R$^3$ may be the same or different and are H or halogen.

Hereinafter the moiety

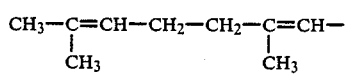

will be expressed as "X" in the structural formulae set out below.

Thus, the following types of compounds are included within the scope of the present invention.

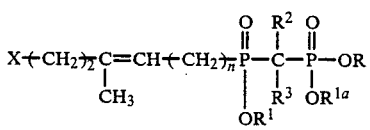

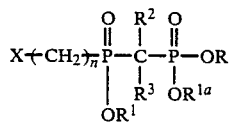

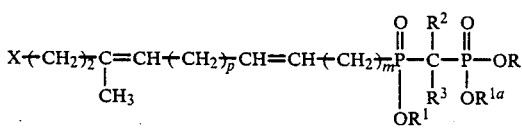

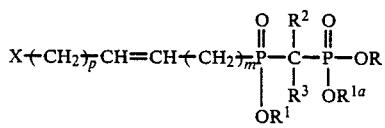

The term "low alkyl" or "alkyl" as employed herein alone or as part of another group includes both straight and branched chain hydrocarbons, containing 1 to 12 carbons in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. The lower alkyl or alkyl group may be substituted with a substituent including a halo-substituent, such as F, Br, Cl or I or CF$_3$, an alkoxy substituent, an aryl substituent, an alkyl-aryl substituent, a haloaryl substituent, a cycloalkyl substituent, an alkyl-cycloalkyl substituent, hydroxy, and alkylamino substituent, an alkanoylamino substituent, an arylcarbonylamino substituent, a nitro substituent, a cyano substituent, a thio substituent or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1, 2 or 3 lower alkyl groups, halogens (Cl, Br or F), 1, 2 or 3 lower alkoxy groups, 1, 2 or 3 hydroxy groups, 1, 2 or 3 phenyl groups, 1, 2 or 3 alkanoyloxy group, 1, 2 or 3 benzoyloxy groups, 1, 2 or 3 haloalkyl groups, 1, 2 or 3 halophenyl groups, 1, 2 or 3 allyl groups, 1, 2 or 3 cycloalkylalkyl groups, 1, 2 or 3 adamantylalkyl groups, 1, 2 or 3 alkylamino groups, 1, 2 or 3 alkanoylamino groups, 1, 2 or 3 arylcarbonylamino groups, 1, 2 or 3 amino groups, 1, 2 or 3 nitro groups, 1, 2 or 3 cyano groups, 1, 2 or 3 thiol groups, and/or 1, 2 or 3 alkylthio groups with the aryl group preferably containing 3 substituents.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy", or "aryloxy" or "aralkoxy" as employed herein alone or as part of another group includes any of the above lower alkyl, alkyl, aralkyl or aryl groups linked to an oxygen atom.

The term "lower alkylthio", "alkylthio", "arylthio" or "aralkylthio" as employed herein alone or as part of another group includes any of the above lower alkyl, alkyl, aralkyl or aryl groups linked to a sulfur atom.

The term "lower alkylamino", "alkylamino", "arylamino", "arylalkylamino" as employed herein alone or as part of another group includes any of the above lower alkyl, alkyl, aryl or arylalkyl groups linked to a nitrogen atom.

The term "alkanoyl" as used herein as part of another group refers to lower alkyl linked to a carbonyl group.

The term "halogen" or "halo" as used herein refers to chlorine, bromine, fluorine, iodine and CF$_3$, with chlorine or fluorine being preferred.

The term "metal ion" refers to alkali metal ions such as sodium, potassium or lithium and alkali earth metal ions such as magnesium.

Preferred are those compounds of formula I which have the following structure

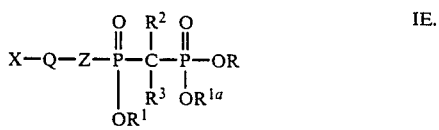

wherein Q is

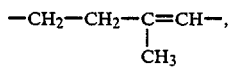

Z is —CH$_2$CH$_2$— or —CH=CH—; R$^2$ and R$^3$ are each H or each F; R, R$^1$ and R$^{1a}$ are OH or metal ions.

The compounds of formula I of the invention may be prepared according to the following reaction sequence and description thereof.

A. Preparation of Compounds of Invention

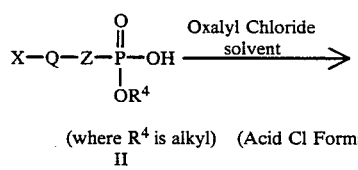

(where R$^4$ is alkyl) (Acid Cl Formation)
II

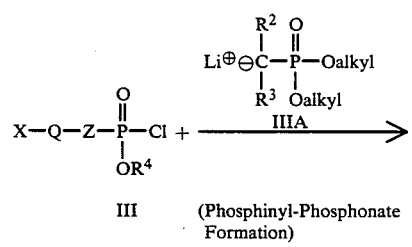

III (Phosphinyl-Phosphonate Formation)

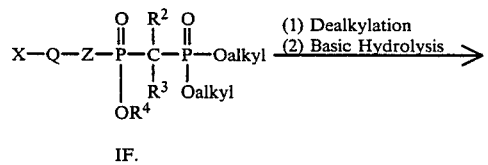

IF.

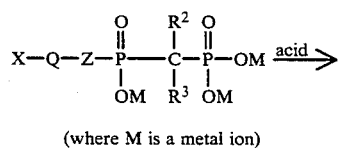

(where M is a metal ion)
IG.

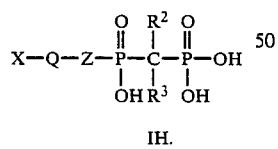

IH.

A(1) Alternative Preparation of Compounds of Invention

|   | (1) Dealkylation |    |
|---|(2) Acid Hydrolysis|   |
| IF. | → | IH. |

B. Preparation of Starting Materials
(1) Where Z is (CH$_2$)$_n$ and n is 1 to 5 or Z is (CH$_2$)$_p$—CH=CH—(CH$_2$)$_m$— and p is 0 to 2 and m is 1 or 2

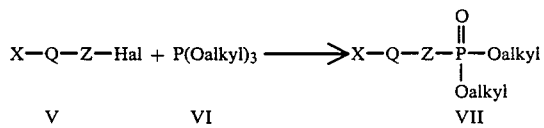

V VI VII
(wherein Hal is a halogen such as Cl, Br or I)

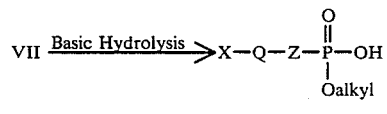

II (2) Where Z is (CH$_2$)$_n$ and n is 2 to 5 or Z is —(CH$_2$)$_p$—CH=CH—(CH$_2$)$_m$— and p is 0 to 2 and m is 2

X—Q—(CH$_2$)$_{n-1}$—Hal
VA
or
X—Q—(CH$_2$)$_p$—CH=CH—(CH$_2$)$_{m-1}$—Hal
VB (wherein Hal is a halogen such as Br or I)

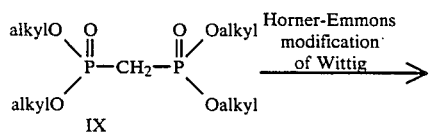

(3) Where Z is (CH$_2$)$_p$—CH=CH—(CH$_2$)$_m$—, p is 0 to 2 and m is o

X—Q—(CH$_2$)$_p$—CHO +
VIII

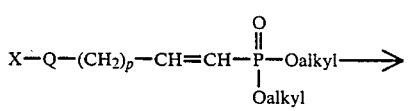

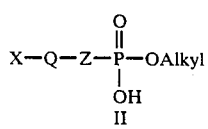

II

As seen in reaction sequence "A", compounds of Formula I may be prepared by treating monoacid II

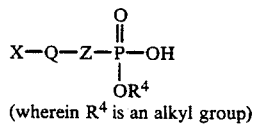

(wherein R⁴ is an alkyl group)

in an aromatic solvent such as benzene or toluene, preferably containing dimethylformamide, or other appropriate inert organic solvent, with oxalyl chloride, and then evaporating the reaction mixture to give acid chloride III

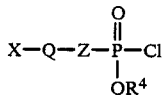

To a stirred solution of an optionally substituted dialkyl methyl phosphonate

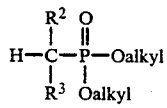

in an inert organic solvent such as tetrahydrofuran cooled to a temperature within the range of from about −90° C. to about 0° C. is added a lithium source, such as n-butyl lithium or lithium diisopropylamide in a hexane or other inert organic solvent under an inert atmosphere such as argon to form the lithium salt IIIA

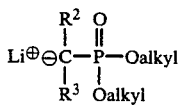

The lithium salt IIIA is maintained at a reduced temperature as described above and acid chloride III in an inert organic solvent such as tetrahydrofuran or ethyl ether is added to form the phosphinyl-phosphonate IF.

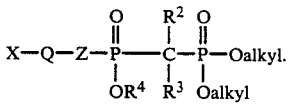

The lithium salt IIIA will be employed in a molar ratio to acid chloride III of within the range of from about 1.8:1 to about 2.5:1 and preferably from about 2.0:1 to about 2.4:1. Ester IF, in an inert organic solvent such as methylene chloride, may then be subjected to dealkylation by treating with bromotrimethylsilane or iodotrimethylsilane in the presence of 2,4,6-collidine or bis(trimethyl)silyltrifluoroacetamide and then treating with a strong inorganic base such as aqueous NaOH, KOH, LiOH or Mg(OH)₂, optionally in the presence of an alcohol such as methyl alcohol, to form the salt IG which may be separated out by chromatography. Salt IG may be treated with a strong acid such as HCl to form acid IH.

Intermediates II and III are novel compounds and thus form a part of the present invention.

As seen in reaction sequence "B", the starting materials II may be prepared as follows.

As seen in reaction scheme B(1), where Z is $(CH_2)_n$ and n is 1 to 5 or Z is $-(CH_2)_p-CH=CH-(CH_2)_m-$ and p is 0, 1 or 2 and m is 1 or 2, starting material II may be prepared by treating halide V

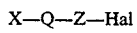    V with trialkyl phosphite VI $P(Oalkyl)_3$    VI under an inert atmosphere, such as argon, at an elevated temperature of within the range of from about 120° to about 165° C. for a period of from about 1 to about 30 hours to form the phosphonic ester compound VII

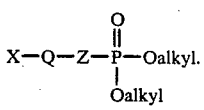    VII

The reaction of phosphite VI and halide V is carried out employing a molar ratio of VI:V of within the range of from about 2:1 to about 50:1.

Phosphonic ester VII is subjected to basic hydrolysis such as by treatment with alkali metal hydroxide such as aqueous KOH or NaOH, optionally in the presence of an alcohol such as methanol, ethanol or isopropanol under an inert atmosphere, such as argon, at reflux temperature to form the phosphonic acid II which is a novel compound and thus forms a part of the present invention.

The starting halides V are either known or are prepared from farnesol or geraniol by conventional means.

As seen in reaction scheme B(2), where in starting material II, Z is $(CH_2)_n$ and n is 2 to 5 or Z is $-(CH_2)_p-CH=CH-(CH_2)_m-$ and p is 0 to 2 and m is 2, II may be prepared by treating halide VA or VB with the salt IIIB such as

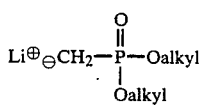    IIIB in the presence of an inert organic solvent such as tetrahydrofuran or ethyl ether at a reduced temperature of within the range of from about −78° to about 0° C. for a period within the range of from about 1 to about 24 hours, to form the phosphonic ester VIIA

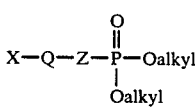    VIIA which is subjected to basic hydrolysis as described above for scheme B(1) to form phosphinic acid starting material II.

The reaction of VA or VB and IIIB is carried out employing a molar ratio of VA or VB:IIIB of about 1:1.

The salt IIIB is formed by treating phosphonate IIIB′

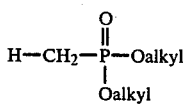 IIIB' in an inert organic solvent such as tetrahydrofuran or ethyl ether under an inert atmosphere such as argon with a source of alkali metal such as n-butyllithium in an inert organic solvent such as hexane.

The starting halides VA or VB are either known or prepared from geraniol or farnesol by conventional means.

As seen in reaction scheme B(3), where in starting material II, Z is $-(CH_2)_p-CH=CH-(CH_2)_m-$ and p is 0 to 2 and m is 0, II may be prepared by employing a Horner-Emmons modification of the Wittig reaction by treating aldehyde VIII

 VIII with tetraalkyl methylenebisphosphonate IX in the presence of sodium hydride and an inert organic solvent such as tetrahydrofuran, toluene or ethyl ether at a temperature within the range of from about $-20°$ to about 25° C. for a period of from about 1 to about 24 hours, to form phosphonic ester X

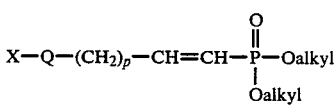

(a novel compound in accordance with the present invention) which is subjected to basic hydrolysis as described in scheme B(1) to form phosphonic acid II.

The reaction of aldehyde VIII and phosphonate IX is carried out employing a molar ratio of VIII:IX of within the range of from about 1:1 to about 1:2.

The aldehyde starting material VIII where Q is a bond and p is O, that is geranial, is a known compound. Where Q is

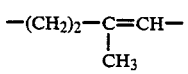

and p is O is farnesal, a known compound.

As will be appreciated by one skilled in the art, other starting aldehydes and starting alcohols are either known in the art or prepared from geraniol or farnesol employing conventional chemical synthesis.

The novel intermediates in accordance with the invention may be defined by the following formula:

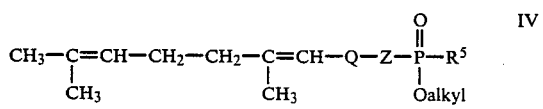 IV wherein $R^5$ is OH or Cl.

The compounds of the present invention are inhibitors of squalene synthetase and thus are useful in inhibiting cholesterol biosynthesis and treating hypercholesterolemia and atherosclerosis. Inhibition of squalene synthetase may be measured by the following procedure.

Rat liver microsomal squalene synthetase activity is measured using farnesyl pyrophosphate as substrate and quantitating squalene synthesis using gas chromatographic analysis. The assay was developed by modifying conditions originally described by Agnew (Methods in Enzymology 110:357, 1985).

Preparation of Rat Liver Microsomes:

Livers are dissected from 2 or 3 decapitated Sprague Dawley rats and are quickly transferred to ice cold buffer (potassium phosphate, 0.05 M, (pH 7.4); $MgCl_2$, 0.004 M; EDTA, 0.001 M; and 2-mercaptoethanol 0.01 M) and rinsed thoroughly. The livers are minced in cold buffer (2.0 ml/g) and homogenized using a Potter-Elvejhem homogenizer. The homogenate is centrifuged at $5,000 \times g$, 10 minutes (4° C.), and the supernatant poured through 2 layers of cheese cloth. The supernatant is then centrifuged at $15,000 \times g$ for 15 minutes (4°). Again the supernatant is filtered through 2 layers of cheese cloth, and centrifuged a third time at $100,000 \times g$ for 1.0 hour at 4° C. Following centrifugation the microsomal pellet is resuspended in a volume of buffer equivalent to 1/5 the volume of the original homogenate, and homogenized in a ground glass homogenizer. Aliquotted microsomes are frozen at $-80°$ C., and retain activity for at least two months.

Enzyme Assay:

Reaction Mixtures are prepared in 50 ml round bottom pyrex glass tubes with tight-fitting, teflon-lined, screw caps. Tubes are cooled to 4° C., and the following components are added in sequence:

| | |
|---|---|
| 1. Potassium phosphate buffer 0.275 M, pH 7.4) | 0.36 ml |
| 2. KF (55 mM) | 0.36 ml |
| 3. NADPH (5.0 mM, freshly prepared) | 0.36 ml |
| 4. $H_2O$ (or $H_2O$ + test compound) | 0.16 ml |
| 5. $MgCl_2$ (27.5 mM) | 0.36 ml |
| 6. Microsomal Enzyme (0.48 mg microsomal protein in homogenization buffer) (15 µl prep. 4/23/86) | 0.20 ml |
| | 1.8 ml |

This mixture is equilibrated under $N_2$ at 4° C. for 5–15 minutes. Reaction mixtures are then warmed to 30° C., and the enzyme reaction initiated by adding 0.2 ml of farnesyl pyrophosphate (21.9 µM) prepared in $H_2O$. Each tube is again overlayered with $N_2$, and incubated at 30° C. for 60 minutes. The reaction is stopped by the addition of 1.0 ml KOH (40%). Ethanol (95%) (spectral grade) (1.0 ml) is added to each tube. Docosane (5 nmoles in hexane) is added to each tube as an internal standard. The mixture is saponified at 65° C. for 30 minutes. The tubes are cooled to room temperature and extracted twice with 10.0 ml spectral grade hexane.

The upper organic phase fractions are pooled in glass 20.0 ml scintillation vials and reduced in volume to $\simeq 1.0$ ml under a stream of $N_2$. The sample is then transferred to acid-washed, conical bottom, glass (1.0 ml) microvials, and brought to dryness under $N_2$. The residue is resuspended in 50 µl hexane (spectral grade), and these samples are spun at 1000 rpm at room temperature for 10 minutes. Following centrifugation approximately 40 µl of supernatant is transferred to 100 µl acid-washed microvials with septa/crimp-top caps (compatible with the Hewlett-Packard GC auto injector).

Gas Chromatography:

Two μL of each sample is injected onto a fused silica megabore DB-17 column (15 M×0.525 mm) (J&W Scientific) using a splitless mode of injection. Gas flow rates are listed below:

| | |
|---|---|
| Make up gas (helium) | 20 ml/min. |
| Air | 400 ml/min. |
| Hydrogen | 30 ml/min. |
| Carrier (helium) | 15 ml/min. |
| Septum purge vent | 5 ml/min. |
| | (Septum purge off 0.00 min., on at 0.5 min.) |

The injector temperature is 200° C., and the FID detector temperature is set at 270° C. Oven temperature is programmed through a two ramp sequence as follows:
Oven:
Initial temperature 180° C., initial time 10 minutes
Ramp one: 20° C./minute
Second temperature 250° C., second time 10 minutes
Ramp two: 20° C./minute
Third temperature 260° C., third time 10 minutes
(Equilibration time 1.0 minute)

Using this gas chromatographic system, docosane (internal standard) has a retention time of 3.6–3.7 minutes, and squalene has a retention time of 14.7–14.9 minutes. The amount of squalene in each reaction mixture is determined by obtaining the areas under the squalene and docosane peaks and using the following formula to calculate the amount of squalene (nmoles) in the total reaction mixture.

$$\text{Squalene (nmoles/reaction mixture)} = \frac{\text{Squalene Peak Area}}{\text{Docasane Peak Area}} \times RR^* \quad (X)$$

5.0 (nmoles docasane internal standard)

*$RR$ = Response Ratio [Docasane/Squalene]
*$RR$ = 0.56

Compounds Testing:

Compounds are dissolved in $H_2O$ and added to reaction mixtures prior to addition of farnesyl pyrophospate substrate. All reaction mixtures are run in duplicate, at several concentrations. Additionally, all compound $I_{50}$ values are derived from composite dose response data with the 95% confidence interval indicated.

A further aspect of the present invention is a pharmaceutical composition consisting of at least one of the compounds of Formula I in association with a pharmaceutical vehicle or diluent. The pharmaceutical compostion can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 200 and 2,000 mg per day, which can be administered in a single dose or in the form of individual doses from 1–4 times per day.

A typical capsule for oral administration contains active ingredient (250 mg), lactose (75 mg) and magnesium stearate (15 mg). The mixture is passed through a 60 mesh sieve and packed into a No. 1 gelatin capsule.

A typical injectible preparation is produced by asceptically placing 250 mg of sterile active ingredient into a vial, aseptically freeze-drying and sealing. For use, the contents of the vial are mixed with 2 ml of physiological saline, to produce an injectible preparation.

The following Examples represent preferred embodiments of the present invention. Unless otherwise indicated, all temperatures are expressed in degrees Centigrade. Purification of final targets was often achieved by chromatography on CHP20P gel (referred to herein as HP-20), a highly porous styrene-divinyl benzene copolymer available from Mitsubishi Chemical Industries. $^{31}P$ NMR spectra were accumulated in the $^{1}H$ decoupled mode, employing 85% $H_3PO_4$ ($\delta = 0$ ppm) as the external reference. For $^{19}F$ NMR spectra, $CF_3CCl_3$ ($\delta = 82.6$ ppm) was employed as an internal reference.

EXAMPLE 1

(E,E)-[[Hydroxy(4,8,12-trimethyl-3,7,11-tridecatrienyl)phosphinyl]methyl]phosphonic acid, tripotassium salt A. (E,E)-3,7,11-Trimethyl-2,6,10-dodecatrienyl bromide A solution of 1.00 g (4.5 mmol) of E,E-farnesol (Aldrich, further purified by flash chromatography) in 10 ml of distilled ether at 0° C. under argon in the dark was treated dropwise with a solution of 195 μL (2.05 mmol, 0.45 eq.) of $PBr_3$ in 2 ml of ether. The resultant mixture was stirred at 0° C. for one hour, then quenched with water and separated. The organic phase was washed with 5 ml of $H_2O$, 5 ml of saturated $NaHCO_3$, and 5 ml of brine, dried over $Na_2SO_4$ and evaporated to give 1.26 (98%) of crude bromide as a clear oil. TLC Silica (2:8 ethyl acetate:Hexane) Rf=0.69 (decomposes).

$^{1}H$ NMR (CDCl$_3$), δ5.52 (t, 1H, J=8.5 Hz), 5.08 (m, 2H), 4.01 (d, 2H), 1.9–2.2 (m, 8H), 1.73 (s, 3H), 1.68 (s, 3H), 1.60 (s, 6H) ppm.

B. (E,E)-(4,8,12-Trimethyl-3,7,11-tridecatrienyl)phosphonic acid, dimethyl ester To a stirred solution of 3.06 g (24.64 mmol) of dimethyl methylphosphonate in 50 ml of THF under argon was added 14.6 ml (23.47 mmol) of 1.60 M n-butyllithium in hexane over 10 minutes to give a white suspension. After stirring for 30 minutes at −78° C., 6.36 g (22.32 mmol) of Part A bromide in 14 ml of THF was added over 10 minutes. The reaction was allowed to stir at −78° C. for one hour, followed by 0° C. for 45 minutes, and was then quenched with excess methanol. Most of the solvent was evaporated and the residue was dissolved in ethyl acetate, washed with water and brine, dried (MgSO$_4$) and evaporated to provide 7.35 g of an oil. The crude material was flash chromatographed on 350 g of silica gel, packed in 75:25 and eluted with 90:10 ethyl acetate: petroleum ether, collecting 70 ml fractions. Fractions 23-72 yielded 5.78 g (72%) of pure title compound as a colorless oil.

TLC Silica gel (EtOAc) Rf=0.21
IR(CCl$_4$) 2967, 2952, 2918, 2852, 1449, 1382, 1250, 1223, 1185, 1065, 1039, 831 cm$^{-1}$.
$^{1}H$ NMR (CDCl$_3$), δ6 5.10 (m, 3H), 3.73 (d, 6H, J=11 Hz), 2.28 (m, 2H), 2.03 (m, 8H), 1.77 (m, 2H), 1.68 (s, 3H), 1.62 (s, 3H), 1.60 (s, 6H) ppm.

Mass Spec (CI-CH$_4$N$_2$O, +ions) m/e 369 (m+C$_3$H$_5$), 357 (M+C$_2$H$_5$), 329 (M+H).

C.
(E,E)-(4,8,12-Trimethyl-3,7,11-tridecatrienyl)phosphonic acid, monomethyl ester A stirred solution of 2.22 g (6.76 mmol) of Part B compound in 10 ml of 1:1 methanol:water containing 4.4 g (68.2 mmol) of potassium hydroxide was heated to 65°-75° C. for 5.5 hours. The methanol was evaporated and the residue was stirred with dichloromethane/water and acidified by adding 10.0 g of solid KHSO$_4$. The mixture was stirred until the phases were homogeneous. The organic layer was washed with dichloromethane. The combined organic extracts were washed with 1:1 brine:water, dried (MgS$_4$) and evaporated to provide 2.13 g (100%) of the title monoacid as a pale yellow oil.

TLC Silica (6:3:1 n-C$_3$H$_7$OH:con NH$_3$:H$_2$O) Rf=0.62

IR(CCl$_4$) 2918, 2853, 1449, 1229, 1193, 1056, 987 cm$^{-1}$ $^1$H NMR (CDCl$_3$), δ 12.22 (s, 1H), 5.10 (m, 3H), 3.72 (d, 3H, J=10.6 Hz), 2.30 (m, 2H), 2.02 (m, 8H), 1.77 (m, 2H), 1.68 (s, 3H), 1.62 (s, 3H), 1.59 (s, 6H) ppm.

Mass Spec (CI-H$_2$O, +ions) m/e 315 (M+H), 179.

D.
(E,E)-[[Hydroxy(4,8,12-trimethyl)-3,7,11-tridecatrienyl)phosphinyl]methyl]phosphonic acid, trimethyl ester To a stirred solution of 2.05 g (6.50 mmol) of Part C monoacid in 20 ml of benzene containing two drops of DMF was added 1.7 ml (19.50 mmol) of oxalyl chloride over 10 minutes at room temperature. After 2.5 hours, the solution was evaporated and the residue was twice dissolved in benzene and evaporated to provide the acid chloride as an orange oil.

To a stirred solution of 1.80 g (14.50 mmol) of dimethyl methylphosphonate in 30 ml of THF at −78° C. was added 8.7 ml (14.0 mmol) of 1.6 M n-butyllithium in hexane over five minutes under argon to provide a white suspension. After stirring for 15 minutes at −78° C., the acid chloride described above was added in 13 ml of THF over five minutes. After one hour at −78° C., the reaction was allowed to warm to 0° C. for one hour and was diluted with ether and quenched with 10% HCl. The ether solution was separated, washed with water, saturated NaHCO$_3$ and brine, dried (MgSO$_4$) and evaporated to give 1.57 g of crude title compound. The combined aqueous layers were back extracted with CH$_2$Cl$_2$ and the organic layer was washed with brine, dried (MgSO$_4$) and evaporated to provide an additional 1.10 g of crude title compound. Flash chromatography on 200 g of silica gel packed in 2:98 and eluted with 4:96 CH$_3$OH:CH$_2$Cl$_2$ gave 565.1 mg (18%) of slightly impure title compound followed by 1.79 g (58%) of pure title compound as a colorless oil.

Rechromatography of the impure fractions gave an additional 225.6 mg (8%) of pure title compound.

TLC Silica (5:95 CH$_3$OH:CH$_2$CL$_2$) Rf=0.22.

IR(CCl$_4$) 2955, 2917, 2853, 1450, 1259, 1240, 1184, 1166, 1064, 1039, 845, 822, 781 cm$^{-1}$.

$^1$H NMR (CDCl$_3$), δ 5.14 (m, 3H), 3.81 (d, 6H, J=11 Hz), 3.77 (d, 3H, J=10.5 Hz), 2.40 (dd, 2H, J=21.1, 16.3 Hz), 2.30 (m, 2H), 2.01 (m, 10H), 1.68 (s, 3H), 1.63 (s, 3H), 1.60 (s, 6H) ppm.

Mass Spec (CI-CH$_4$/N$_2$O, +ions) m/e 393 (M+C$_3$H$_5$), 381 (M+C$_2$H$_5$), 353 (M+H).

E.
(E,E)-[Hydroxy(4,8,12-trimethyl-3,7,11-tridecatrienyl)phosphinyl]methyl]phosphonic acid, tripotassium salt To a stirred solution of 1.475 g (3.51 mmol) of Part D title compound in 20 ml of CH$_2$Cl$_2$ at 0° C. under argon was added 0.93 ml (7.02 mmol) of 2,4,6-collidine followed by 1.90 ml (14.4 mmol) of bromotrimethylsilane, dropwise over 10 minutes. After one hour at 0° C., the reaction was allowed to warm to room temperature for 5.5 hours. The solution was evaporated and pumped at high vacuum, and the residue was dissolved in 20 ml of methanol for 20 minutes. After evaporation of the solvent, the residue was redissolved in 20 ml of methanol and treated with 11.0 ml (11.0 mmol) of 1M KOH. Most of the solvent was evaporated and the aqueous solution was applied to a 2.5 cm diameter×16.0 cm length column of HP-20. The column was eluted with pure water (fractions 1–30) followed by a gradient ranging from 100% H$_2$O to 100% acetonitrile. Approximately 10 ml fractions were collected every two minutes. Fractions 12–38 gave a lyophilate, which was further dried under vacuum over P$_2$O$_5$ to provide 1.12 g (65%) of an off-white lyophilate. This material was determined to be title tri-potassium salt, which gave a solution of pH 9–9.5 in water. TLC Cellulose (7:2:1 n-C$_3$H$_7$OH:con NH$_3$:H$_2$O) Rf=0.54.

IR(KBr) 3415, 2968, 2928, 2858, 1660, 1449, 1383, 1161, 1107, 1077, 1043, 973, 799 cm$^{-1}$.

$^1$H NMR (CD$_3$OD:D$_2$O 1:1), δ 5.20, 5.08, 5,06 (three t, 1H each, J=7Hz), 2.22 (m, 2H), 1.9–2.1 (m, 10H), 1.64 (s, 3H), 1.62 (s, 3H), 1.56 (s, 6H) ppm.

$^{31}$P NMR (CD$_3$OD:D$_2$O 1:1) δ 43.9 (d, J$_{pp}$δ8 Hz, CPC) 17.2 (d, J$_{pp}$δ8 Hz, CPO$_3$) ppm.

Mass Spec (FAB, + ions) m/e 531 (M+K), 493 (M+H), 455 (M+2H-K)

Anal Calcd for C$_{17}$H$_{29}$O$_5$P$_2$K$_3$: C, 38.13; H, 6.36; P, 11.60. Found: C, 37.58; H, 6.19; P, 11.47.

EXAMPLE 2
(E,E)-[Difluoro[hydroxy(4,8,12-trimethyl-3,7,11-tridecatrienyl)phosphinyl]methyl]phosphonic acid, tripotassium salt A. (Difluoromethyl)phosphonic acid, diethyl ester A modification of the literature procedure was followed: L. Z. Soborovski, *J. Gen. Chem. USSR*, 1959, 29, 1115.

A sample of 6.82 g (171 mmol) of 60% NaH in mineral oil was washed twice with 30 ml of petroleum ether and was suspended in 130 ml of THF under argon. A solution of 22 ml (171 mmol) of diethyl phosphite was added dropwise over 45 minutes and the exotherm was controlled with a water bath. After stirring for an additional hour, 42 g (490 mmol) of chlorodifluoromethane was bubbled through the solution over 4.5 hours, while the internal temperature was maintained between 25° and 35° C. with a cool water bath. The white suspension was allowed to stir overnight, was diluted with hexane and filtered through Celite. The filtrate was evaporated to provide 27.6 g of a crude, pale yellow liquid. The crude material was fractionally distilled at 10 mm to provide 5.21 g (16%) of impure title compound (b.p. 82°-84° C.), followed by 20.66 g (64%) of title compound (b.p. 84°-86° C.) as a colorless liquid which contains a trace of impurity.

¹H NMR (CDCl₃), δ 5.93 (td, 1H, $J_{HP}$=27 Hz, $J_{HF}$=49 Hz), 4.29 (quint, 4H, J=7.5 Hz), 1.39 (t, 6H, J=7.5 Hz) ppm.

¹³C NMR(CDCl₃), δ 109.2 (td, $J_{CP}$=214 Hz, $J_{CF}$=257 Hz), 63.9 (d, $J_{CP}$=7.6 Hz), 15.7 (d, $J_{CP}$=3.8 Hz) ppm.

Mass Spec (CI-CH₄/N₂O, + ions) m/e 217 (M+C₂H₅), 206 (M+NH₄), 189 (M+H), 163, 135.

B.
(E,E)-[Difluoro[methoxy(4,8,12-trimethyl-3,7,11-tridecatrienyl)phosphinyl]methyl]phosphonic acid, diethyl ester To a stirred solution of 1.02 g (3.23 mmol) of Example 1, Part C mono-acid in 15 ml of benzene was added 0.85 ml (9.69 mmol) of oxalyl chloride over five minutes with much gas evolution. After 40 minutes, a drop of DMF was added, resulting in additional gas evolution, followed one hour later with another drop of DMF, resulting in no gas evolution. The solvent was evaporated, and the residue was twice redissolved in benzene and re-evaporated, and then placed under high vacuum until use.

To a solution of 0.54 ml (3.88 mmol) of diisopropylamine in 6 ml of THF at −78° C. was added 2.2 ml (3.55 mmol) of 1.6 M n-butyllithium in hexanes over five minutes. After warming to 0° C. for 10 minutes and recooling to −78° C., a solution of 640 mg (3.40 mmol) of Part A compound in 4 ml of THF was added over five minutes. The yellow anion was allowed to stir for 30 minutes at −78° C., and then the acid chloride described above was added in 5 ml of THF over five minutes. The reaction was allowed to stir at −78° C. for two hours, and was stored at −85° C. in a freezer for 16 hours. The reaction was quenched with 0.2 ml (3.50 mmol) of acetic acid in 4 ml of ether, followed by dilution with ether and acidification with 10% HCl. The ether layer was washed with water and brine, dried and evaporated to give 1.56 g of a yellow liquid.

The crude product was flash chromatographed on 70 g of silica gel eluted with 40:60 ethyl acetate:hexane to provide 698.1 mg (45%) of a colorless oil. NMR indicates that this material was contaminated with 17 mol % of Part A compound, corrected yield 42%.

TLC Silica gel (ethyl acetate) Rf=0.34

IR(CCl₄) 2983, 2963, 2931, 2918, 2857, 1444, 1272, 1254, 1049, 985 cm⁻¹

¹H NMR (CDCl₃), δ 5.10 (m, 3H), 4.36 (m, 4H), 3.92 (d, 3H, J=10.6 Hz), 2.36 (m, 2H), 2.03 (m, 10H), 1.68 (s, 3H), 1.63 (s, 3H), 1.60 (s, 6H), 1.41 (t, 6H, J=7 Hz) ppm.

Mass Spec (CI-CH₄/N₂O, +ions) m/e 514 (M+C₂H₅), 485 (M+H).

C.
(E,E)-[Difluoro[hydroxy(4,8,12-trimethyl-3,7,11-tridecatrienyl)phosphinyl]methyl]phosphonic acid, tripotassium salt To a solution of 565 mg (1.17 mmol) of Part C compound in 8 ml of dry methylene chloride under argon in the dark was added 0.62 ml (2.33 mmol) of (bis-trimethylsilyl)trifluoroacetamide and the reaction was allowed to stir for ten minutes. After cooling to 0° C., 0.67 ml (4.70 mmol) of iodotrimethylsilane was added to give a golden solution. The reaction was allowed to stir for 80 minutes at 0° C., the solvents were evaporated and the residue was dissolved in benzene and re-evaporated. The dark orange liquid was pumped at high vacuum, and was treated with a solution of 1 ml (7.0 mmol) of triethylamine in 9 ml of methanol, yielding a colorless solution. After 15 minutes, the methanol was evaporated and the residue was dissolved in 4 ml of water and basified with 4.7 ml of 1 M KOH. The solution was reduced in volume to about 4 ml and the mixture was flash chromatographed on HP-20 eluted with a water acetonitrile gradient to give 574 mg of impure material. This was rechromatographed on a 2.5 cm diameter, 20 cm length column of HP-20, eluted with pure water (fractions 1–20), followed by the gradient addition of 600 ml of methanol to a 500 ml reservoir of water, collecting approximately 20 ml fractions. Fractions 49–64 were combined to give after lyophilization, 508 mg (82%) of title compound as a white powder. This product was a hydroscopic, variable hydrate. The pH of a 1% w/v solution of title compound was 7.8.

TLC Silica gel (6:3:1 n-C₃H₇OH:con NH₃:H₂O), Rf=0.31

EM Cellulose (7:2:1 n-C₃H₇OH:con NH₃:H₂O), Rf=0.64

IR(KBr) 3500, 3200, 2968, 2924, 1215, 1132, 1102, 1051, 999, 954 cm⁻¹.

¹H NMR (D₂O), δ 5.24 (t, 1H, J=6.6 Hz), 5.16, 5.18 (two overlapping t, 2H total, J=7 Hz), 2.22 (m, 2H), 1.98, 2.06 (m, 8H), 1.77 (m, 2H), 1.64 (s, 3H), 1.61 (s, 3H), 1.57 (s, 6H) ppm.

¹⁹F NMR (D₂O) δ120.3 (t, $J_{PF}$=75 Hz) ppm.

³¹F NMR (D₂O), δ 32.8 (td, $J_{PF}$=75 Hz, $J_{PP}$=46 Hz), 4.07 (td, $J_{PF}$=75 Hz, $J_{PP}$=46 Hz) ppm.

Mass Spec (FAB, +ions) m/e 567 (M+K), 529 (M+H), 429 (M+2H-K).

Anal Calcd for C₁₇H₂₇F₂O₅P₂K₃: C, 38.62; H, 5.15; F, 7.19; P, 11.72.

*Found: C, 38.70; H, 5.49; F, 7.19; P, 11.50.

*Analytical sample was dried at 50° C. for 2 hours under vacuum.

EXAMPLE 3
(E,E,E)-[Hydroxy(4,8,12-trimethyl-1,3,7,11-tridecatetraenyl)phosphinyl]methyl]phosphonic acid, mixture of di- and tri-potassium salts

A. E,E-Farnesal

To a stirred solution of 2.5 ml (28.7 mmol) of distilled oxalyl chloride in 50 ml of dry CH₂Cl₂ at −60° C. was added 4.2 ml (58.5 mmol) of DMSO in 10 ml of CH₂Cl₂ over 6 minutes between −60° and −55° C. with much gas evolution. After 7 minutes at −60° C., a solution of 5.0 g (22.50 mmol) of E,E-farnesol in 14 ml of CH₂Cl₂ was added over 15 minutes to give a thick white suspension. After 20 minutes at −65° C., 19 ml (136 mmol) of triethylamine was added over 7 minutes and 5 minutes later the cold bath was removed and the reaction was allowed to warm to room temperature over 50 minutes. The mixture was diluted with 400 ml of ether, washed with two 50 ml portions each of water and brine, dried over MgSO₄, and evaporated. The residue was taken up in ether, filtered to remove some insoluble solid, and evaporated to provide 5.06 g (100%) of crude E,E-farnesal, contaminated with a trace of the 2Z-isomer.

TLC Silica gel (20:80 ethyl acetate:Hexane) Rf=0.38.

¹H NMR(CDCl₃), δ 10.00 (d, 1H, J=8 Hz), 5.88 (d, 1H, J=8 Hz), 5.09 (m, 2H), 2.24 (m, 4H), 2.17 (s, 3H), 2.01 (m, 4H), 1.68 (s, 3H), 1.62 (s, 6H) ppm.

B.
(E,E,E)-(4,8,12-Trimethyl-1,3,7,11-trideca-tetraenyl)phosphonic acid, dimethyl ester A 1.0 g (25.0 mmol) sample of 60% sodium hydride in mineral oil was washed with two 20 ml portions of pentane, and suspended in 50 ml of THF. A solution of 5.80 g (25.0 mmol) of the tetramethyl methylenebisphosphonate (Lancaster Synthesis #5847) in 12 ml of THF was added dropwise over 15 minutes at 0° C. The reaction was allowed to warm to room temperature for 20 minutes to give a clear solution. Part A aldehyde (4.97 g, 22.5 mmol) in 14 ml of THF was added over 10 minutes and the reaction was allowed to stir for 1.5 hours at room temperature. Upon dilution with ether, the solution was washed twice with water and once with brine, dried over MgSO$_4$, and evaporated to provide 7.05 g of a yellow oil. $^1$H-NMR and TLC indicated that the desired title product was contaminated with the 1E,3Z-isomer set out below.

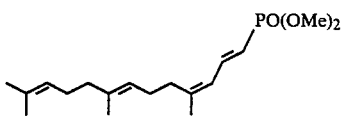

(1E,3Z,7E,11E)-(4,8,12-trimethyl-1,3,7,11-trideca-tetraenyl)phosphonic acid, dimethyl ester)

The crude product was partially purified by flash chromatography on silica gel, eluted with 50:50 ethyl acetate:hexane, and the crossover fractions were rechromatographed eluting with 25:75 followed by 75:25 ethyl acetate:hexane. This procedure provided 0.946 g (13%) of the 1E,3Z-isomer and 5.29 g (72%) of the desired title 1E,3E-isomer.

TLC Silica gel (ethyl acetate) title isomer: Rf=0.28. 1E,3Z-isomer: Rf=0.39

IR(CCl$_4$) 2968, 2951, 2928, 2919, 2851, 1640, 1589, 1448, 1385, 1254, 1237, 1185, 1062, 1036, 987, 867, 832, 792, 774, 554 cm$^{-1}$.

$^1$H NMR(CDCl$_3$), δ 7.39 (ddd, 1H, J=21, 17, 11 Hz), 5.97 (d, 1H, J=11 Hz), 5.51 (dd, 1H, J=20, 17 Hz), 5.08 (m, 2H, H$_4$), 3.72 (d, 6H, J=11 Hz), 2.15 (m, 4H), 2.00 (m, 4H), 1.88 (s, 3H), 1.68 (s, 3H), 1.60 (s, 6H) ppm.

Mass spec (CI-CH$_4$/N$_2$O, +ions) m/e 367 (M+C$_3$H$_5$), 355 (M+C$_2$H$_5$), 327 (M+H).

C.
(E,E,E)-(4,8,12-Trimethyl-1,3,7,11-trideca-tetraenyl)phosphonic acid, monomethyl ester A solution of 2.43 g (7.44 mmol) Part B diester in 40 ml of methanol was treated with 30 ml of 1 M KOH and heated to 65° C. for 5 hours. The pH was adjusted to 7.5 with 10% HCl and the methanol was evaporated. The aqueous residue was made strongly acidic with 10% HCl and was extracted with two portions of ethyl acetate. The organic layer was washed with water and brine, dried over MgSO$_4$, and evaporated to provide 2.33 g (100% crude) title acid in the form of a pale yellow liquid.

TLC Silica gel (7:2:1 n-C$_3$H$_7$OH:con NH$_3$:H$_2$O) Rf=0.46.

IR(CCl$_4$) 2969, 2926, 2917, 2852, 1641, 1591, 1448, 1240, 1206, 1053, 984 cm$^{-1}$.

$^1$H NMR(CDCl$_3$), δ 11.91 (s, 1H), 7.33 (ddd, 1H, J=21, 17, 11 Hz), 5.94 (d, 1H, J=11 Hz), 5.59 (dd, 1H, J=20.5, 11 Hz), 3.69 (d, 3H, J=11.6 Hz), 2.13 (m, 4H), 2.02 (m, 4H), 1.86 (s, 3H), 1.67 (s, 3H), 1.60 (s, 6H) ppm.

Mass Spec (CI-CH$_4$/N$_2$O, +ions) m/e 341 (M+C$_3$H$_5$), 313 (M+H)

D.
(E,E,E)-[[Hydroxy(4,8,12-trimethyl-1,3,7,11-tridecatetraenyl)phosphinyl]methyl]phosphonic acid, trimethyl ester A sample of 2.41 g (7.72 mmol) of Part C acid was evaporated with three portions of benzene, dissolved in 25 ml of benzene containing 30 μl (0.344 mmol) of DMF, and 2.10 ml (24.10 mmol) of distilled oxalyl chloride was added over 10 minutes with much gas evolution. After 2.5 hours at room temperature, an additional drop of DMF was added, causing additional gas evolution. The solution was stirred for 30 minutes, the solvents were evaporated, the residue was evaporated twice with benzene and the resulting orange oil was dried under vacuum until employed below.

To a solution of 2.10 g (16.98 mmol) of dimethyl methylphosphonate in 30 ml of THF at −78° C. under argon was added 10.4 ml (16.6 mmol) of 1.6 M n-butyllithium in hexane over 10 minutes to give a white suspension. After stirring for 30 minutes, a solution of the acid chloride described above in 13 ml of THF was added over 10 minutes. The reaction was allowed to stir for 2 hours at −78° C., then quenched with saturated NH$_4$Cl and allowed to warm to room temperature. The mixture was extracted with ethyl acetate, and the organic layer was washed with 1:1 water:brine followed by brine, dried over MgSO$_4$, and evaporated to provide 3.54 g of a yellow oil. The crude product was flash chromatographed on silica gel eluting with 2:98 methanol:methylene chloride to provide 2.29 g (71%) of a pale yellow oil. Although this material was homogeneous by TLC, $^{13}$C-NMR indicated that it contained a minor impurity. The impure material was rechromatographed on 200 g of silica gel eluted with 2:98 methanol:methylene chloride collecting 40 ml fractions. Fractions 28-37 gave 1.33 g of title compound enriched in the impurity, and fractions 38-53 gave 0.725 g of title compound containing just a trace of the impurity. The latter material was employed in the next step.

TLC Silica gel (5:95 CH$_3$OH:CH$_2$Cl$_2$) Rf=0.15

IR(film) 2958, 2924, 2855, 1638, 1450, 1384, 1241, 1186, 1121, 1108, 1033, 845, 819 cm$^{-1}$.

$^1$H NMR(CDCl$_3$), δ 7.47 (ddd, 1H, J=20, 17, 11 Hz), 6.02 (d, 1H, J=11 Hz), 5.78 (dd, 1H, J=25, 17 Hz), 5.09 (m, 2H), 3.81 (d, 3H, J=9.5 Hz), 3.77 (d, 3H, J=9 Hz), 3.75 (d, 3H, J=9 Hz), 2.48 (m, 2H), 2.15 (m, 4H), 2.02 (m, 4H), 1.90 (s, 3H), 1.68 (s, 3H), 1.60 (s, 6H) ppm.

Mass Spec (CI-CH$_4$/N$_2$O+ions) m/e 447 (M+C$_2$H$_5$), 419 (M+H).

E.
(E,E,E)-[Hydroxy(4,8,12-trimethyl-1,3,7,11-tridecatetraenyl)phosphinyl]methyl]phosphonic acid, mixture of di- and tri-potassium salts To a stirred solution of 725.5 mg (1.73 mmol) of Part D compound and 0.46 ml (3.48 mmol) of 2,4,6-collidine in 8 ml of methylene chloride at 0° C. was added 0.91 ml (6.90 mmol) of bromotrimethylsilane over 5 minutes to give a cloudy mixture. After 5 minutes at 0° C., the reaction was allowed to warm to room temperature for 2 hours to provide a pale yellow solution. The solution was evaporated, and the residue was placed under high vacuum and then dissolved in 6.9 ml of 1 M KOH in 10 ml of methanol. After 10 minutes, the methanol and some of the water was evaporated and the aqueous solution was applied to a 2.5 cm diameter, 20 cm height column of HP-20 packed in water. The column was eluted with water (fractions 1–14) followed by a gradient created by the gradual addition of acetonitrile to water, collecting 10 to 15 ml fractions. The desired product eluted in fractions 21–33, with a pH ranging from 11 to 7.5, indicating that the di- and tri- potassium salts were eluting without separation. These fractions were combined, the acetonitrile was evaporated and the aqueous solution was lyophilized to give 743 mg of a white, sticky powder. Further drying over $P_2O_5$ under vacuum provided 664.7 mg (81%) of title product in the form of a white lyophilate. A 1% w/v solution of title product in water was measured to be pH 8.65. The title product was very hydroscopic and exists as a variable hydrate. Analytical data on a sample of title product dried to constant weight indicated this material was a 1.5:1 mixture of di- and tri-potassium salts.

TLC Cellulose (7:2:1 n-$C_3H_7OH$:con $NH_3$:$H_2O$) Rf=0.54.

IR(KBr) 3400, 2968, 2924, 1641, 1449, 1383, 1236, 1174, 1154, 1127, 1109, 1079, 969, 886, 792, 517 $cm^{-1}$.

$^1$H NMR($D_2O$), δ 7.04 (td, 1H, $J_t$=18, $J_d$=11 Hz), 5.97 (d, 1H, J=11 Hz), 5.95 (dd, 1H, J=22, 18 Hz), 5.11 (m, 2H), 2.11 (s, 4H), 1.9–2.1 (m, 6H), 1.81 (s, 3H), 1.63 (s, 3H), 1.57 (s, 3H), 1.56 (s, 3H) ppm.

$^{31}$P-NMR ($D_2O$),

δ 25.6 (d, J=5 Hz), 12.4 (d, J=5 Hz) ppm.

Mass Spec (FAB+ions) m/e 529 (M+4K-3H), 491 (M+3K-2H), 453 (M+2K-H). M=376 (molecular weight of triacid).

Anal Calcd for $C_{17}H_{27.6}P_2K_{2.4}$: C, 43.65; H, 5.95; P. 13.24.

*Found: C, 43.78; H, 6.47; P. 13.36.

*Sample was dried to constant weight under vacuum at 50° C.

EXAMPLE 4

(E,E,E)-[Difluoro[hydroxy(4,8,12-trimethyl-1,3,7,11-tridecatetraenyl)phosphinyl]methyl]phosphonic acid, tripotassium salt

A.

[Difluoro[methoxy(4,8,12-trimethyl-1,3,7,11-tridecatetraenyl)phosphinyl]methyl]phosphonic acid, diethyl ester To a stirred solution of 1.09 g (3.48 mmol) of Example 3 Part C phosphonic acid in 6 ml of dichloromethane under argon was added 1.3 ml (7 mmol) of diethyl(trimethylsilyl)amine. The reaction was allowed to stir for two hours at room temperature, evaporated, reevaporated with benzene, and pumped under high vacuum. The residue was dissolved in 8 ml of dichloromethane and two drops of DMF at 0° C., and 0.5 ml (5.73 mmol) of oxalyl chloride was added over ten minutes. The residue was allowed to stir at 0° C. for 75 minutes followed by room temperature for 45 minutes. The solution was evaporated, evaporated with benzene and pumped at high vacuum to give a dark oil with some suspended solid.

To a solution of 0.59 ml (4.18 mmol) of distilled diisopropylamine in 7 ml of THF at −78° C. under argon was added dropwise 2.4 ml (3.84 mmol) of 1.6 M n-butyllithium in hexane. The reaction was allowed to warm to 0° C. for 15 minutes, followed by recooling to −78° C. A solution of 691 mg (3.67 mmol) of diethyl difluoromethanephosphonate (prepared as described in Example 2 Part A) in 4 ml of THF was added over ten minutes. The pale yellow solution was allowed to stir for 30 minutes at −78° C. and the above-described chloride was added in 4 ml of THF over 10 minutes. The dark solution was maintained at −78° C. for 1.5 hours and then placed in a −85° C. freezer for 15 hours. The reaction was quenched with 0.3 ml of acetic acid in 4 ml of ether and allowed to warm to room temperature. The mixture was partitioned between ether and 10% HCl, and the ether layer was washed with water and saturated $NaHCO_3$. The combined aqueous layers were extracted with two portions of dichloromethane, and the combined organic layers were dried ($MgSO_4$) and evaporated to provide 1.62 g of an orange oil. The crude product was flash chromatographed twice on silica gel, eluting with 45:55 ethyl acetate:petroleum ether in the first and 10:90 THF:toluene in the second column, to provide 511.1 mg (30%) of a pale yellow liquid. $^1$H NMR spectroscopy indicates that this material is contaminated with 5% of an impurity, whose spectral data is consistent with the following structure

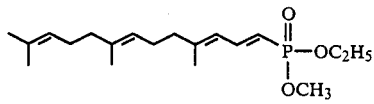

TLC Silica gel (35:65 THF:toluene) Rf=0.39 (title compound), Rf=0.31 (impurity).

$^1$H NMR($CDCl_3$), δ 7.56 (ddd, 1H, J=20, 17, 11 Hz), 6.06 (d, 1H, J=11 Hz), 5.72 (dd, 1H, J=25, 17 Hz), 4.35 (m, 4H), 3.93 (d, 3H, J=10 Hz), 1.9–2.3 (m, 8H), 1.92 (s, 3H), 1.68 (s, 3H), 1.60 (s, 6H) ppm.

Mass Spec (CI-$CH_4$, +ions) m/e 483 (M+H, title compound), 341 (M+H, impurity).

B.

(E,E,E)-[Difluoro[hydroxy(4,8,12-trimethyl-1,3,7,11-tridecatetraenyl)phosphinyl]methyl]phosphonic acid, tripotassium salt A sample of 434.7 mg (0.901 mmol) of Part A compound was evaporated with benzene and then dissolved in 6 ml of dry dichloromethane at 0° C. To this solution was added 0.24 ml (1.82 mmol) of 2,4,6-collidine followed by 0.50 ml (3.81 mmol) of iodotrimethylsilane, dropwise over five minutes. The reaction was allowed to stir at 0° C. for 2.5 hours and was then evaporated and the residue was pumped at high vacuum. Aqueous potassium hydroxide (3.2 ml of a 1 M solution) was added and the solution was freeze-dried. The tan powder was dissolved in a minimum amount of water and chromatographed at medium pressure on a 2.5 cm diameter, 22 cm height column of HP-20 packed in water. The column was eluted with a gradient created by the gradual addition of 800 ml of 75:25 methanol:water to 600 ml of water, collecting 10–15 ml fractions. Fractions 42–61 were combined and lyophilized to provide 349.3 mg (74%) of title compound as a hydroscopic white powder, which was dried further under high vacuum. A 1% w/v solution of title compound in water was pH 8.75.

TLC silica gel (6:3:1 n-$C_3H_7OH$:con $NH_3$:$H_2O$) Rf=0.31.

IR(KBr) 3300, 2972, 2924, 2854, 1640, 1218, 1199, 1118, 1045, 997, 553, 530 $cm^{-1}$.

$^1$H NMR ($D_2O$), δ 7.22 (td, 1H, J=17, 11 Hz), 6.07 (d, 1H, J=11 Hz), 5.93 (dd, 1H, J=17, 22 Hz), 5.17 (m,

2H), 2.17 (s, 4H), 2.10 (q, 2H, J=7 Hz), 2.02 (t, 2H, J=7 Hz), 1.87 (s, 3H), 1.68 (s, 3H), 1.61–1.62 (two s, 3H each) ppm.

$^{31}$P NMR (D$_2$O), δ 21.5 (td, J$_{PP}$=47 Hz, J$_{PF}$=81 Hz), 4.90 (td, J$_{PP}$=47 Hz, J$_{PF}$=74 Hz) ppm.

Mass Spec (FAB, +ions) m/e 565 (M+K), 527 (M+H), 489 (M-K+2H), 309, 271, 246, 217, 208, 157.

Anal Calcd for C$_{17}$H$_{25}$F$_2$O$_5$K$_3$P$_2$: C, 38.77; H, 4.79; F, 7.22; P, 11.76.

*Found: C, 38.89; H, 4.82; F. 7.32; P, 11.87. *Sample was dried to constant weight at 50° C. before the analysis.

EXAMPLE 5

(E,E)-[[Hydroxy(4,8,12-trimethyl-3,7,11-tridecatrienyl)phosphinyl]methyl]phosphonic acid, monomethyl ester, disodium salt An emulsion of 333.2 mg (0.79 mmol) of Example 1 Part D triester in 3.95 ml (3.95 mmol, 5 eq.) of 1M NaOH was stirred at 50° C. under nitrogen for 16 hours, then cooled. The amber solution was loaded onto a 2.5 cm diameter×16 cm height column of HP-20 packed with water. The column was eluted with a gradient created by the gradual addition of 450 ml of acetonitrile to 450 ml of H$_2$O. Approximately 10 ml fractions were collected every two minutes. Fractions 24–28 were combined and lyophilized, and the white lyophilate was further dried under high vacuum overnight to afford 206.4 mg (60%) of title product.

TLC Silica gel (7:2:1 n-C$_3$H$_7$OH:con.NH$_3$:H$_2$O) Rf=0.30.

IR(KBr) 3427, 3282, 2966, 2924, 2854, 1218, 1172, 1146, 1102, 1064, 790, 747 cm$^{-1}$.

$^1$H NMR (D$_2$O), δ 5.24 (m, 1H), 5.16 (m, 2H), 3.55 (d, 3H, J$_{HP}$=11 Hz), 2.20 (m, 2H), 2.0–2.2 (m, 10H), 1.67 (s, 3H), 1.65 (s, 3H), 1.60 (s, 6H) ppm.

Mass Spec (FAB, +ions) m/e 437 (M+H), 415 (M+2H-Na).

Anal Calcd for C$_{18}$H$_{32}$O$_5$P$_2$·Na$_2$: C, 49.54; H, 7.39; P, 14.20. *Found: C, 49.78; H, 7.62; P, 14.49. *Sample was dried to constant weight at 50° C.

EXAMPLE 6

(E,E)-[[Hydroxy(5,9,13-trimethyl-4,8,12-tetradecatrienyl)phosphinyl]methyl]phosphonic acid, trisodium salt

A. Bishomofarnesyl bromide (1) (E,E)-5,9,13-Trimethyl-4,8,12-tetradecatrienoic acid, 1,1-dimethylethyl ester To a solution of 9.60 ml (68.5 mmol, 1.5 eq.) of diisopropylamine in 100 ml of THF at −78° C. under argon was added 28.2 ml (45.0 mmol, 1.0 eq.) of 1.6M nBuLi in hexanes over 20 minutes. After warming to 0° C. for 15 minutes, the solution was recooled to −78° C. and 6.05 ml (45 mmol, 1.0 eq.) of t-butyl acetate was added over 20 minutes. After an additional 15 minutes, 16.0 ml (92 mmol, 2.05 eq.) of hexamethyl phosphoric triamide (HMPA) was added, followed by a solution of 12.53 g (45.0 mmol) of Example 1 Part A farnesyl bromide in 100 ml of THF over 20 minutes. The reaction was stirred at −78° C. for 2.5 hours, quenched with saturated NH$_4$Cl, and allowed to warm to room temperature. After diluting with 400 ml of ethyl acetate, the mixture was washed with four 100 ml portions of water, and 200 ml of brine, dried over MgSO$_4$ and evaporated to provide 12.96 g of crude product as a yellow oil. Purification by flash chromatography on 1000 g of silica gel, eluted with 1:9 ethyl acetate:petroleum ether afforded 9.39 g (65%) of title compound as a pale yellow oil.

TLC Silica gel (2:98 ethyl acetate:hexane) Rf=0.16
IR(neat) 2977, 2925, 2857, 1733, 1452, 1368, 1258, 1149 cm$^{-1}$.

$^1$H NMR (CDCl$_3$), δ 5.10 (m, 3H), 2.25 (m, 4H), 1.9–2.1 (m, 8 H), 1.68 (s, 3H), 1.62 (s, 3H), 1.59 (s, 6H), 1.44 (s, 9H) ppm.

Mass Spec (CI-CH$_4$/N$_2$O)(+ions) m/e 265 (M+H-C$_4$H$_8$), 247, 183, 137, 68, 57. (−ions) m/e 319 (M-H), 279, 251, 100.

(2) Bishomofarnesol

To a stirred solution of 5.00 g (15.6 mmol) of Part A compound in 45 ml of dry ether at 0° C. under argon was added 592 mg (15.6 mmol, 1 mol-eq.) of lithium aluminum hydride, and the resulting suspension was stirred at room temperature for 20 hours. After cooling to 0° C., the reaction was quenched by treating with 5 ml of H$_2$O, 5 ml of 15% NaOH, and 15 ml of H$_2$O and the suspension was stirred for ½ hour. After adding Na$_2$SO$_4$, the slurry was filtered through Celite, the solids were washed well with ether, and the filtrate was evaporated to obtain 3.62 g of crude product. Purification by flash chromatography on 300 g of silica gel eluted with 1:9 ethyl acetate:petroleum ether provided 3.516 g (90%) of bishomofarnesol as a colorless liquid.

TLC Silica gel (2:8 ethyl acetate:hexane) Rf=0.19.
IR(neat) 3330, 2964, 2926, 2873, 2858, 1448, 1384, 1107, 1059, 401 cm$^{-1}$. $^1$H NMR (CDCl$_3$), δ 5.10 (m, 3H), 3.63 (t, 2H, J=6.5 Hz), 1.9–2.2 (m, 10H), 1.68 (s, 3H), 1.62 (s, 3H), 1.60 (s, 6H) ppm.

Mass Spec (CI-CH$_4$/N$_2$O, +ions) m/e 251 (M+H), 249 (M+H-H$_2$), 137, 123, 109, 69.

(3) (E,E)-5,9,13-Trimethyl-4,8,12-tetradecatrien-1-ol, methylsulfonate ester

To a stirred solution of 2.02 g (8.07 mmol) of Part (2) alcohol in 20 ml of dichloromethane at 0° C. was added 2.2 ml (16.1 mmol) of triethylamine followed by 0.69 ml (8.90 mmol) of methanesulfonyl chloride, dropwise over 15 minutes. After stirring for 1.5 hours at 0° C., the reaction was diluted with dichloromethane, washed with 20 ml each of 10% HCl, saturated NaHCO$_3$ and brine, dried (MgSO$_4$) and evaporated to give 2.71 g ("100%") of the crude title mesylate as a colorless oil.

TLC Silica gel (CH$_2$Cl$_2$) Rf=0.46
$^1$H NMR(CDCl$_3$), δ 5.09 (t, 3H, J=6.5 Hz), 4.21 (t, 2H, J=7.0 Hz), 2.99 (s, 3H), 1.9–2.2 (m, 10H), 1.78 (quint, 2H, J=7.0 Hz), 1.65 (s, 3H), 1.61 (s, 3H), 1.60 (s, 6H) ppm.

(4) Bishomofarnesyl bromide

To a solution of 2.56 g (7.79 mmol) of Part (3) mesylate in 15 ml of THF at room temperature was added 2.02 g (23.37 mmol) of anhydrous lithium bromide, resulting in a mild exotherm. For this purpose, lithium bromide was dried at 100° C. over P$_2$O$_5$ under vacuum. The suspension was allowed to stir for 23 hours at room temperature, when it was diluted with ether, washed with water (two portions) and brine, dried (MgSO$_4$) and evaporated to provide 2.29 g of a pale yellow liquid. Flash chromatography on 65 g of silica gel eluted with petroleum ether gave 2.22 g (91%) of title bromide as a colorless liquid.

TLC Silica gel (hexane) Rf=0.35 IR(neat) 2965, 2926, 2856, 1666, 1440, 1383, 1249, 1109 cm$^{-1}$. $^1$H NMR(CDCl$_3$), (270 MHz), δ 6 5.10 (br, 3H), 3.39 (t, 2H, J=6.5 Hz), 1.8-2.3 (m, 12H), 1.68 (s, 3H), 1.63 (s, 3H), 1.60 (s, 6H) ppm.

B.
(E,E)-(5,9,13-Trimethyl-4,8,12-tetradecatrienyl)phosphonic acid, diethyl ester A mixture of 1.121 g, (3.57 mmol) of Part A bishomofarnesyl bromide and 12.3 ml (71.5 mmol, 20 eq.) of triethylphosphite under argon was stirred at 140°-150° C. for 20 hours. After cooling, the triethylphosphite was distilled off under high vacuum. The crude product was combined with that from a previous reaction on 1.11 mmol of bishomofarnesylbromide and purified by flash chromatography on 180 g of silica, eluted with 1:1 ethyl acetate:petroleum ether to obtain 1.63 g (94%) of title compound.

TLC Silica gel (ethyl acetate) Rf=0.36.

IR(CCl$_4$ solution) 2980, 2930, 2914, 2874, 2857, 1444, 1390, 1241, 1164, 1098, 1061, 1034, 959, 778, 746 cm$^{-1}$.

$^1$H NMR (CDCl$_3$), δ4.99 (m, 3H), 4.00 (m, 4H), 1.8-2.1 (m, 10H), 1.57 (s, 3H), 1.50 (s, 9H), 1.4-1.6 (m, 4H), 1.22 (t, 6H, J=7.0 Hz) ppm.

Mass Spec (CI-i-butane/N$_2$O, +ions) m/e 371 (M+H).

C.
(E,E)-(5,9,13-Trimethyl-4,8,12-tetradecatrienyl)phosphonic acid, monoethyl ester An emulsion of 1.62 g (4.32 mmol) of Part B compound in a mixture of 10.8 ml (43.2 mmol, 10 eq.) of 4 M KOH and 10.8 ml of ethanol was stirred under argon at reflux for 20 hours. After cooling, the solution was neutralized to pH 6.5 with 10% HCl and ethanol was removed under vacuum. The residue was diluted with 200 ml ethyl acetate, made strongly acidic with 10% HCl, and separated. The aqueous phase was extracted with 200 ml ethyl acetate. The combined organic layers were washed with 50 ml brine, dried over MgSO$_4$ and evaporated for a crude yield of 1.42 g (96%) of a pale yellow oil.

TLC Silica gel (7:2:1 n-C$_3$H$_7$OH:con. NH :H$_2$O) Rf=0.52

IR(CCl$_4$) 2978, 2971, 2929, 2916, 2856, 2300, 1446, 1222, 1051, 983, 796 cm$^{-1}$.

$^1$H NMR(CDCl$_3$), δ 11.48 (br s, 1H), 5.06 (br, 3H), 4.04 (quint, 2H, J$_{HH}$=J$_{HP}$=7.0 Hz), 1.9-2.1 (m, 10H), 1.64 (s, 3H), 1.56 (s, 9H), 1.29 (t, 3H, J=7.0 Hz) ppm.

Mass Spec (CI-i-butane/N$_2$O, +ions) m/e 685 (2M+H), 343 (M+H).

D.
(E,E)-[[Ethoxy(5,9,13-trimethyl-4,8,12-tetradecatrienyl)phosphinyl]methyl]phosphonic acid, dimethyl ester A solution of 1.41 g (4.09 mmol) of Part C phosphonic acid in 12.5 ml of dry CH$_2$Cl$_2$ at room temperature under argon was treated with 1.55 ml (8.18 mmol, 2.0 eq.) of N,N-diethyltrimethylsilylamine and stirred for two hours. The solvent was evaporated, the residue was twice dissolved in benzene and reevaporated, and the residue was pump dried for ½ hours.

A mixture of the trimethylsilyl ester prepared above and two drops of DMF in 12.5 ml of CH$_2$Cl$_2$ under N$_2$ at 0° C. was treated dropwise over 20 minutes with 645 μL (7.36 mmol, 1.8 eq.) of oxalyl chloride, then stirred for 45 minutes at 0° C. and one hour at room temperature. The solvent was evaporated, the residue was twice dissolved in benzene and re-evaporated, and the residue was pump dried for ½ hour.

A solution of 886 μL (8.18 mmol, 2.0 eq.) of dimethyl methylphosphonate in 17 ml of THF at −78° C. under argon was treated with 5.6 ml (9.00 mmol, 2.2 eq.) of 1.6M n-BuLi in hexanes. After the thick white suspension had stirred for 30 minutes, the acid chloride prepared above in 5 ml of THF was added in rapid drops. The solution was stirred for two hours at −78° C., quenched with 10 ml of saturated NH$_4$Cl and 5 ml of H$_2$O and allowed to warm to room temperature. The mixture was extracted with four 75 ml portions of CH$_2$Cl$_2$. The combined organic layers were washed with 75 ml of brine, dried over MgSO$_4$ and evaporated to yield 2.52 g of a yellow oil.

Purification by flash chromatography on 250 g of silica gel, eluted with 2:98 CH$_3$OH:CH$_2$Cl$_2$ provide 1.23 g (67%) of title compound as a colorless oil.

TLC Silica gel (7:93 CH$_3$OH:CH$_2$Dl$_2$) Rf=0.21

IR(CCl$_4$) 2955, 2929, 2854, 1449, 1384, 1368, 1259, 1234, 1184, 1164, 1063, 1037, 955, 843, 821, 780, 753, 499 cm$^{-1}$.

$^1$H NMR(CDCl$_3$), δ 5.20 (m, 3H), 4.13 (m, 2H), 3.80 (d, 6H, J$_{HP}$=10.5 Hz), 2.29 (dd, 2H, J$_{HP}$=16.0, 21.0 Hz), 1.8-2.1 (m, 12H), 1.68 (s, 3H), 1.60 (s, 9H), 1.34 (t, 3H, J=7.0 Hz) ppm.

Mass Spec (CI-CH$_4$, +ions) m/e 447 (M+C$_2$H$_5$), 449 (M+H), 417 (M+H-CH$_3$OH).

E.
(E,E)-[[Hydroxy(5,9,13-trimethyl-4,8,12-tetradecatrienyl)phosphinylmethyl]phosphonic acid, trisodium salt A solution of 196.4 mg (0.44 mmol) of Part D triester and 87 μL (0.66 mmol, 1.5 eq.) of 2,4,6-collidine in 1.0 ml of dry CH$_2$Cl$_2$ under nitrogen at room temperature was treated with 260 μl (1.98 mmol, 4.5 eq.) of bromotrimethylsilane and stirred for six hours. After evaporating the solvent, the residue was stirred in 2.00 ml (2.00 mmol, 4.5 eq.) of 1M NaOH for 15 minutes and lyophilized overnight. The crude product was dissolved in 2 ml of H$_2$O and loaded onto a 2.5 cm diameter×12 cm height column of HP-20 packed in H$_2$O. The column was eluted with water (fractions 1-20), followed by a gradient created by the gradual addition of acetonitrile to water, collecting approximately 10 ml fractions every two minutes. The desired product eluted in fractions 36-39. These fractions were combined and lyophilized, and the white lyophilate was further dried under pump-vacuum overnight to obtain 143.0 mg (71%) of title product. A 1.0% w/v solution in H$_2$O had a pH of 7.35.

TLC cellulose (7:2:1 n-C$_3$H$_7$OH:con.NH$_3$:H$_2$O) Rf=0.56.

IR(KBr) 3500, 2966, 2926, 2858, 1449, 1380, 1155, 1094, 1062, 976, 896, 829, 795, 443 cm$^{-1}$.

$^1$H NMR(D$_2$O:CD$_3$OD 1:1), δ 5.19 (t, 1H, J=6.5 Hz), 5.09 (m, 2H), 1.9-2.2 (m, 12H), 1.66 (s, 3H), 1.60 (s, 3H), 1.58 (s, 6H) ppm.

$^{31}$P-NMR (D$_2$O), δ 39.6 (d, J=5.0 Hz), 14.4 (d, J=5.0 Hz) ppm.

Mass Spec (FAB, +ions) m/e 481 (M +Na), 459 (M+H), 437, 419.

Anal Calcd for C$_{18}$H$_{31}$O$_5$P$_2$·Na$_3$: C, 47.17; H, 6.82; P, 13.52.

*Found: C, 47.57; H, 7.14; P, 13.67.

*Analytical sample was dried to a constant weight at 50° C.

EXAMPLE 7

(E,E)-[[(4,8-Dimethyl-1,3,7-nonatrienyl)hydroxyphosphinyl]methyl]phosphonic acid, trisodium salt

A. E,E-Geranial

To a stirred solution of 3.75 ml (43.0 mmol, 1.25 eq.) of oxalyl chloride in 80 ml of dry $CH_2Cl_2$ at −60° C. was added a solution of 6.35 ml (89.4 mmol, 2.6 eq.) of DMSO in 15 ml of $CH_2Cl_2$ over 20 minutes with much gas evolution. After 10 minutes at −60° C., a solution of 5.95 ml (34.3 mmol) of geraniol (Aldrich 16,333-3) in 15 ml of $CH_2Cl_2$ was added over 30 minutes to give a white suspension. After 20 minutes at −60° C., 29 ml (206 mmol, 6 eq.) of triethylamine was added over 15 minutes and the reaction was allowed to warm to room temperature over one hour. The mixture was diluted with 350 ml of ether, washed with two 75 ml portions of $H_2O$ and two 75 ml portions of brine, dried over $MgSO_4$ and evaporated to provide 5.53 g (100%) of crude E,E-geranial.

TLC Silica gel (2:8 ethyl acetate:Hexane) Rf=0.37

$^1H$ NMR (CDCl$_3$), δ 9.99 (d, 1H, J=8.0 Hz), 5.88 (d, 1H, J=8.5 Hz), 5.08 (m, 1H), 2.17 (m, 4H), 2.16 (s, 3H), 1.69 (s, 3H), 1.61 (s, 3H) ppm.

B. (E,E)-(4,8-Dimethyl-1,3,7-nonatrienyl)phosphonic acid, dimethyl ester

A 1.53 g (3.82 mmol, 1.11 eq.) sample of 60% sodium hydride in mineral oil was washed with three 20 ml portions of pentane and suspended in 80 ml of THF. A solution of 8.32 g (38.2 mmol, 1.11 eq.) of tetramethyl methylenebisphosphonate (Lancaster Synthesis, #5847) in 15 ml of THF was added dropwise over 20 minutes at room temperature under argon to give a clear solution. Part A aldehyde (5.41 g, 3.44 mmol) in 20 ml of THF was added dropwise over 15 minutes, and the reaction was allowed to stir for 1.5 hours at room temperature before quenching with water. Upon dilution with 350 ml of ether the solution was washed with two 75 ml portions of $H_2O$ and 75 ml of brine, dried over $MgSO_4$ and evaporated to yield 8.24 g of a yellow oil. Purification by flash chromatography on 800 g of Merck 9385 silica, eluted with 1:1 ethyl acetate:petroleum ether provided 4.745 g (53%) of the desired title 1E, 3E-isomer as well as 217.7 mg (3%) of the 1Z,3E isomer set out below.

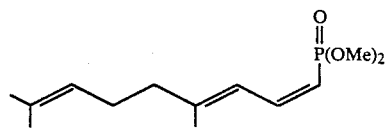

TLC Silica gel (ethyl acetate) title Isomer Rf=0.36. Isomer impurity Rf=0.44.

Data for title isomer:

IR(CCl$_4$) 2970, 2950, 2931, 2917, 2851, 1640, 1588, 1448, 1383, 1253, 1238, 1185, 1104, 1061, 1036, 986, 869, 831, 555, 541, 495 cm$^{-1}$.

$^1H$ NMR(CDCl$_3$), δ7.39 (ddd, 1H, J=21.0, 17.0, 11.5 Hz), 5.97 (d, 1H, J=11.5 Hz), 5.52 (dd, 1H, J=20.0, 17.0 Hz), 5.07 (br, 1H), 3.72 (d, 6H, J=11 Hz), 2.14 (m, 4H), 1.88 (s, 3H), 1.68 (s, 3H), 1.60 (s, 3H) ppm.

Mass Spec (CI-CH$_4$/N$_2$O, +ions) m/e 299 (M+C$_3$H$_5$), 287 (M+C$_2$H$_5$), 259 (M+H), 227 (M+H-CH$_3$OH).

C. (E,E)-(4,8-Dimethyl-1,3,7-nonatrienyl)phosphonic acid, monomethyl ester

A solution of 2.20 g (8.52 mmol) of Part B diester in 50 ml of methanol under nitrogen was treated with 34 ml (34 mmol, 4.0 eq.) of 1 M KOH and the resultant solution was stirred at 65° C. for four hours. After cooling to room temperature, the pH was adjusted to 7.0 with 10% HCl and the methanol was evaporated. The aqueous residue was made strongly acidic with 10% HCl and was extracted with two 100 ml portions of ethyl acetate. The organic layer was washed with 50 ml of $H_2O$, and 50 ml of brine, dried over $MgSO_4$ and evaporated to provide 2.087 g (1005% crude) of title compound in the form of a pale yellow oil.

TLC Silica gel (7:2:1 n-C$_3$H$_7$OH:con. NH$_3$:H$_2$O) Rf=0.47.

IR(CCl$_4$) 2970, 2949, 2929, 2917, 2815, 2333, 1640, 1590, 1448, 1239, 1206, 1052, 984, 870 cm$^{-1}$.

$^1H$ NMR(CDCl$_3$), δ 11.52 (s, 1H), 7.33 (ddd, 1H, J=21.0, 16.5, 11.0 Hz), 5.94 (d, 1H, J=11.0 Hz), 5.60 (dd, 1H, J=21.0, 16.5 Hz), 5.07 (br, 1H), 3.69 (d, 3H, J=11.5 Hz), 2.12 (m, 4H), 1.86 (s, 3H), 1.68 (s, 3H), 1.60 (s, 3H) ppm.

D. (E,E)-[[(4,8-Dimethyl-1,3,7-nonatrienyl)hydroxyphosphinyl]methyl]phosphonic acid, trimethyl ester A solution of 1.99 g (8.15 mmol) of Part C phosphonic acid in 25 ml of dry $CH_2Cl_2$ at room temperature under argon was treated with 3.10 ml (16.3 mmol, 2.0 eq.) of N,N-diethyltrimethylsilylamine and stirred for two hours. The solvent was evaporated, the residue was evaporated twice with benzene and the resulting yellow oil was dried under vacuum for 0.5 hour.

The sample of silyl ester in a solution of 25 ml of dry $CH_2Cl_2$ and two drops of DMF at 0° C. under argon was treated over 0.5 hour with 1.28 ml (14.7 mmol, 1.8 eq.) of oxalyl chloride. After one hour at room temperature, the solvents were evaporated, the residue was evaporated twice with benzene, and the resulting dark brown oil was dried under vacuum for 0.5 hour.

To a solution of 1.80 ml (16.3 mmol, 2.0 eq.) of dimethyl methylphosphonate in 35 ml of THF at −78° C. under argon was added 11.5 ml (17.9 mmole, 2.2 eq.) of 1.6 M n-BuLi in hexane over ten minutes. After stirring for 30 minutes, a solution of the chloride in 10 ml of THF was added over ten minutes. The reaction was allowed to stir for two hours at −78° C., then quenched with saturated NH$_4$Cl and allowed to warm to room temperature. The mixture was extracted with four 150 ml portions of $CH_2Cl_2$ and the organic layer was washed with 75 ml each of 1:1 brine:H$_2$O and brine, dried over $MgSO_4$ and evaporated to obtain 3.28 g of an amber oil. Purification by flash chromatography on 300 g of silica gel eluted with 3:97 CH$_3$OH:CH$_2$Cl$_2$ provided 1.149 g (40%) of pure title triester as well as 545 mg (19%) of nearly pure title triester.

TLC Silica gel (5:95 CH$_3$OH:CH$_2$Cl$_2$) Rf=0.17

IR(CCl$_4$) 2954, 1258, 1241, 1184, 1064, 1037, 849, 822 cm$^{-1}$.

$^1H$ NMR(CDCl$_3$), δ 7.47 (ddd, 1H, J=20, 17, 11 Hz), 6.02 (d, 1H, J=11 Hz), 5.79 (dd, 1H, J=17, 25 Hz), 5.07 (br, 1H), 3.80 (d, 3H, J=11.5 Hz), 3.77 (d, 3H, J=11.5

Hz), 3.72 (d, 3H, J=11.5 Hz), 2.48 (m, 2H), 2.15 (m, 4H), 1.89 (s, 3H), 1.68 (s, 3H), 1.61 (s, 3H) ppm.

Mass Spec (CI -CH$_4$/N$_2$O, +ions) m/e 391 (M+C$_3$H$_5$), 379 (M+C$_2$H$_5$), 351 (M+H), 319 (M+H - CH$_3$OH)

E.
(E,E)-[[(4,8-Dimethyl-1,3,7-nonatrienyl)hydroxyphosphinyl]methyl]phosphonic acid, trisodium salt A solution of 400.3 mg (1.14 mmol) of Part D triester and 225 μL (1.71 mmol, 1.5 eq.) of 2,4,6-collidine in 5 ml of CH$_2$Cl$_2$ at room temperature under argon was treated dropwise with 605 μL (4.57 mmol, 4.0 eq.) of bromotrimethylsilane. The resultant mixture was stirred for five hours, then evaporated and pump-dried for 0.5 hour. The residue was adjusted to pH 12 with 1 M NaOH (approximately 3.45 ml), stirred ten minutes, and lyophilized overnight. The brown lyophilate was dissolved in 3 ml of H$_2$O and applied to a 2.5 cm diameter × 16 cm height column of HP-20 packed and eluted with water. Approximately 10 ml fractions were collected every 1.7 minutes. Fractions 13-19 were combined and lyophilized, them pump-dried for hours to obtain 312.1 mg (73%) of title product in the form of a faintly pink, very flocculent lyophilate. A 1.0% w/v solution of title product has a pH 9.45.

TLC cellulose (7:2:1 n-C$_3$H$_7$OH:con. NH$_3$:H$_2$O) Rf=0.42

IR(KBr) 3390, 2969, 2925, 2858, 1640, 1380, 1236, 1152, 1088, 976, 885, 862, 790, 722, 522 cm$^{-1}$.

$^1$H NMR(D$_2$O), δ7.03 (td, 1H, J=17.0, 11.0 Hz), 6.03 (dd, 1H, J=17.0, 22.0 Hz), 6.01 (d, 1H, J=11.0 Hz), 5.16 (m, 1H), 2.13 (br, 4H), 1.95 (t, 2H, J=18.5 Hz), 1.82 (s, 3H), 1.65 (s, 3H), 1.60 (s, 3H) ppm.

$^{31}$P-NMR(D$_2$O), δ 28.3 (d, J=4.8 Hz), 12.3 (d, J=4.8 Hz) ppm.

Mass Spec (FAB, +ions) m/e 397 (M+Na), 375 (M+H), 353 (M+2H-Na), 331 (M+3H-2 Na).

Anal Calcd for C$_{12}$H$_{19}$O$_{P2}$·Na$_3$: C, 38.52; H, 5.12; P, 16.55.

*Found: C, 38.96; H, 5.45; P, 17.11.

*Sample was dried to constant weight at 50° C.

EXAMPLES 8 TO 18

Following the procedures of Examples 1 to 7, the following additional compounds may be prepared in accordance with the present invention.

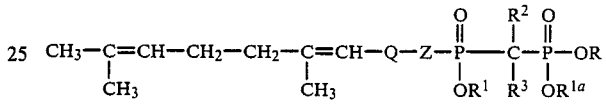

| Ex. No. | Q | Z | R$^2$ | R$^3$ | R | R$^1$ |
|---|---|---|---|---|---|---|
| 8. | —(CH$_2$)$_2$—C(CH$_3$)=CH— | —CH$_2$— | H | H | K | K |
| 9. | bond | —(CH$_2$)$_2$— | F | F | Na | Na |
| 10. | —(CH$_2$)$_2$—C(CH$_3$)=CH— | —(CH$_2$)$_2$— | Cl | Cl | Na | Na |
| 11. | —(CH$_2$)$_2$—C(CH$_3$)=CH— | —(CH$_2$)$_2$— | H | Cl | Na | Na |
| 12. | —(CH$_2$)$_2$—C(CH$_3$)=CH— | —(CH$_2$)$_2$— | F | H | K | K |
| 13. | —(CH$_2$)$_2$—C(CH$_3$)=CH— | —CH=CH—CH$_2$— | H | H | CH$_3$ | K |
| 14. | —(CH$_2$)$_2$—C(CH$_3$)=CH— | —CH=CH— | H | F | Na | Na |
| 15. | bond | —(CH$_2$)$_2$— | H | H | K | K |
| 16. | —(CH$_2$)$_2$—C(CH$_3$)=CH— | —CH$_2$—CH=CH—(CH$_2$)$_2$— | F | H | H | Mg |

| Ex. No. | Q | Z | $R^2$ | $R^3$ | R | $R^1$ |
|---|---|---|---|---|---|---|
| 17. | 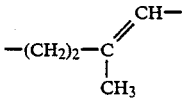 | $-(CH_2)_2-CH=CH-(CH_2)_2-$ | Cl | Cl | K | K |
| 18. | 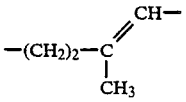 | $-(CH_2)_2-CH=CH-$ | H | H | K | K |
What is claimed is:
1. A compound having the structure
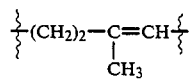
wherein
$R^5$ is OH or Cl and
Q is
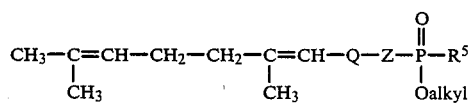
or a bond; and
Z is $-(CH_2)_n-$ or $-(CH_2)_p-CH=CH-(CH_2)_m-$, wherein n is 1 to 5; p is 0, 1 or 2; m is 0, 1 or 2.
2. The compound as defined in claim 1 wherein $R^5$ is OH.
3. This compound as defined in claim 1 wherein $R^5$ is Cl.
* * * * *